(12) United States Patent
Gilad et al.

(10) Patent No.: US 7,896,805 B2
(45) Date of Patent: Mar. 1, 2011

(54) IN-VIVO IMAGING DEVICE AND OPTICAL SYSTEM THEREOF

(75) Inventors: Zvika Gilad, Haifa (IL); Amit Pascal, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 1136 days.

(21) Appl. No.: 11/601,831

(22) Filed: Nov. 20, 2006

(65) Prior Publication Data

US 2007/0118018 A1 May 24, 2007

Related U.S. Application Data

(60) Provisional application No. 60/738,972, filed on Nov. 23, 2005.

(51) Int. Cl.
*A61B 1/06* (2006.01)

(52) U.S. Cl. ......................................... 600/176; 600/160

(58) Field of Classification Search ................... 600/109, 600/117, 118, 160, 176
See application file for complete search history.

(56) References Cited

U.S. PATENT DOCUMENTS

| | | | |
|---|---|---|---|
| 4,278,077 A | 7/1981 | Mizumoto | |
| 5,604,531 A * | 2/1997 | Iddan et al. | 348/76 |
| 5,993,378 A | 11/1999 | Lemelson | |
| 6,038,079 A | 3/2000 | Michaels | |
| 6,142,630 A | 11/2000 | Koester | |
| 6,240,312 B1 | 5/2001 | Alfano et al. | |
| 6,476,851 B1 * | 11/2002 | Nakamura | 348/65 |
| 6,711,304 B2 | 3/2004 | White | |
| 2001/0035902 A1 * | 11/2001 | Iddan et al. | 348/76 |
| 2002/0103417 A1 | 8/2002 | Gazdzinski | |
| 2003/0117491 A1 | 6/2003 | Avni et al. | |
| 2003/0158503 A1 * | 8/2003 | Matsumoto | 600/593 |
| 2005/0054901 A1 * | 3/2005 | Yoshino | 600/176 |
| 2005/0054902 A1 * | 3/2005 | Konno | 600/176 |
| 2005/0124858 A1 * | 6/2005 | Matsuzawa et al. | 600/176 |
| 2006/0030752 A1 * | 2/2006 | Orihara | 600/109 |
| 2007/0217042 A1 * | 9/2007 | Kweon | 359/850 |

FOREIGN PATENT DOCUMENTS

| | | |
|---|---|---|
| DE | 344 0177 | 11/1984 |
| JP | 1992-144533 | 5/1992 |

OTHER PUBLICATIONS

Schwartz, J., et al. "Magnification endoscopy, chromoendoscopy and other novel techniques in evaluation of patients with IBD" Techniques in Gastrointestinal Endoscopy, vol. 6, Iss.4, Oct. 2004, pp. 182-188.*
Feng Gong, Paul Swain, Timothy Mills, Wireless endoscopy, Gastrointestinal Endoscopy, vol. 51, Issue 6, Jun. 2000, pp. 725-729, ISSN 0016-5107, DOI: 10.1067/mge.2000.105724. (http://www.sciencedirect.com/science/article/B6WFY-49YDGN6-N/2/db4eb25c5605386638d9b502c65c2dd4).*
European Search Report of Application EP 06 82 1566 mailed on Dec. 14, 2009.
Search Report of International Application No. PCT/IL2006/001342 mailed on Jan. 30, 2009.

* cited by examiner

*Primary Examiner* — Philip R Smith
(74) *Attorney, Agent, or Firm* — Pearl Cohen Zedek Latzer, LLP

(57) ABSTRACT

The present invention provides an in-vivo imaging device comprising at least one imager and an associated optical system, at least the optical system located in an optical dome of the imaging device, the optical dome having a tip, the optical system comprising an optical lens, the optical system having a given effective focal length f, the optical lens being located at a distance D' from the tip; wherein $D'/f \geqq 6$.

5 Claims, 3 Drawing Sheets

IN-VIVO IMAGING DEVICE AND OPTICAL SYSTEM THEREOF

CROSS REFERENCE TO RELATED APPLICATIONS

This application claims the benefit of U.S. Provisional Application No. 60/738,972, filed on Nov. 23, 2005, entitled "IN-VIVO IMAGING DEVICE AND OPTICAL SYSTEM THEREOF", which is hereby incorporated by reference.

FIELD OF THE INVENTION

The present invention relates to an in-vivo imaging device, specifically an imaging device with an improved optical design.

BACKGROUND OF THE INVENTION

Known devices may be helpful in providing in-vivo imaging. Autonomous in-vivo imaging devices, such as swallowable or ingestible capsules or other devices may move through a body lumen, imaging as they move along. Some of these devices use a wireless connection to transmit image data. Current in-vivo imaging devices provide imaging capabilities that may be limited to specific body lumens. Different optical designs may be needed to conform to the variable sizes of body lumens.

SUMMARY OF THE INVENTION

In accordance with the present invention, there is provided an in-vivo imaging device comprising at least one imager and an associated optical system, at least the optical system located in an optical dome of the imaging device, the optical dome having a tip, the optical system comprising an optical lens, the optical system having a given effective focal length f, the optical lens being located at a distance D' from the tip; wherein $D'/f \geq 6$.

According to some embodiments, the at least one imager comprises a pixel array, each pixel having a given pixel size, b, wherein $b/f=0.01$ radians.

According to some embodiments, the at least one imager comprises a pixel array, each pixel having a given pixel size, b, wherein b/f is in the range 0.01−0.0015 to 0.01+0.0015 radians.

According to some embodiments, the optical system comprises first, second and third optical lenses and an aperture stop.

According to some embodiments, the first optical lens is an objective lens and is located at the distance D' from the tip.

According to some embodiments, the aperture stop is located between the first and second optical lenses and the third optical lens is located between the second optical lens and the at least one imager.

BRIEF DESCRIPTION OF THE DRAWINGS

The present invention will be understood and appreciated more fully from the following detailed description taken in conjunction with the appended drawings in which.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

It is noted that some embodiments of the present invention may be directed to an autonomous, typically ingestible in-vivo device. Other embodiments need not be ingestible. Devices or systems according to embodiments of the present invention may be similar to embodiments described in International Application WO 01/65995 and/or in U.S. Pat. No. 5,604,531, each of which are assigned to the common assignee of the present invention and each of which are hereby fully incorporated by reference. Furthermore, a receiving and/or display system suitable for use with embodiments of the present invention may also be similar to embodiments described in WO 01/65995 and/or in U.S. Pat. No. 5,604,531. Devices and systems as described herein may have other configurations and other sets of components.

Figure 1:
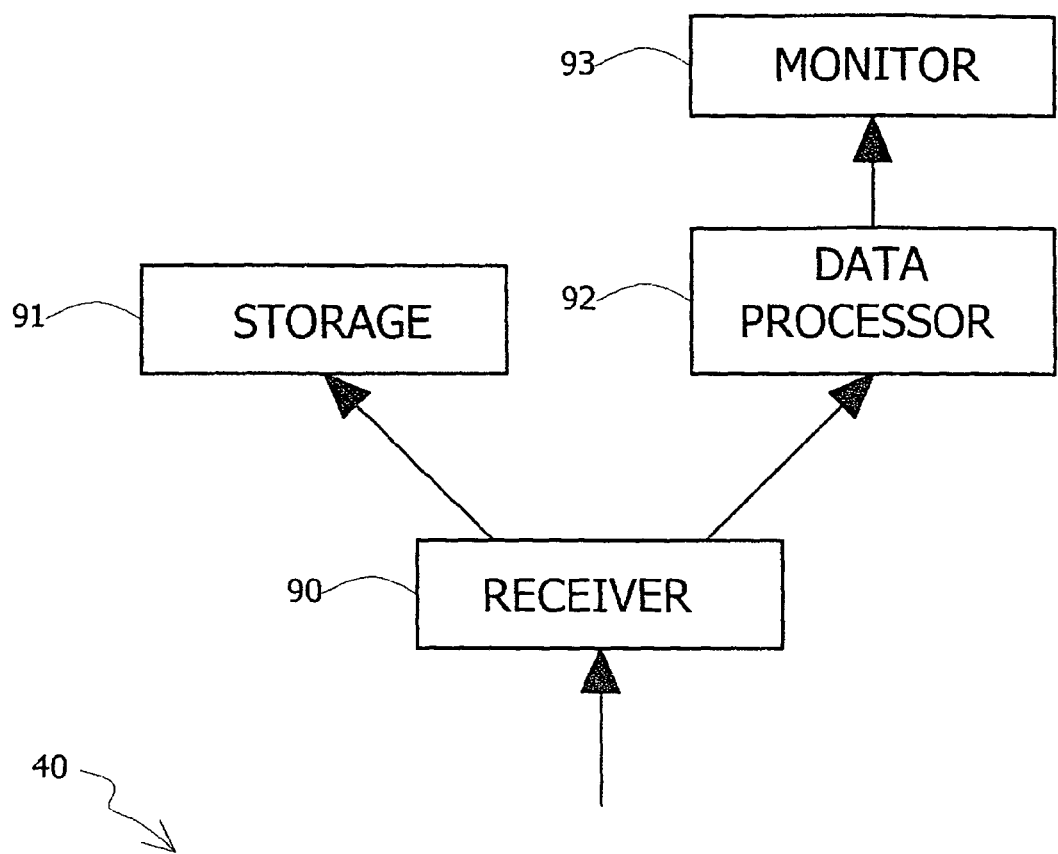
FIG. 1 schematically illustrates an in vivo imaging system and device according to some embodiments of the present invention.
Figure 1:
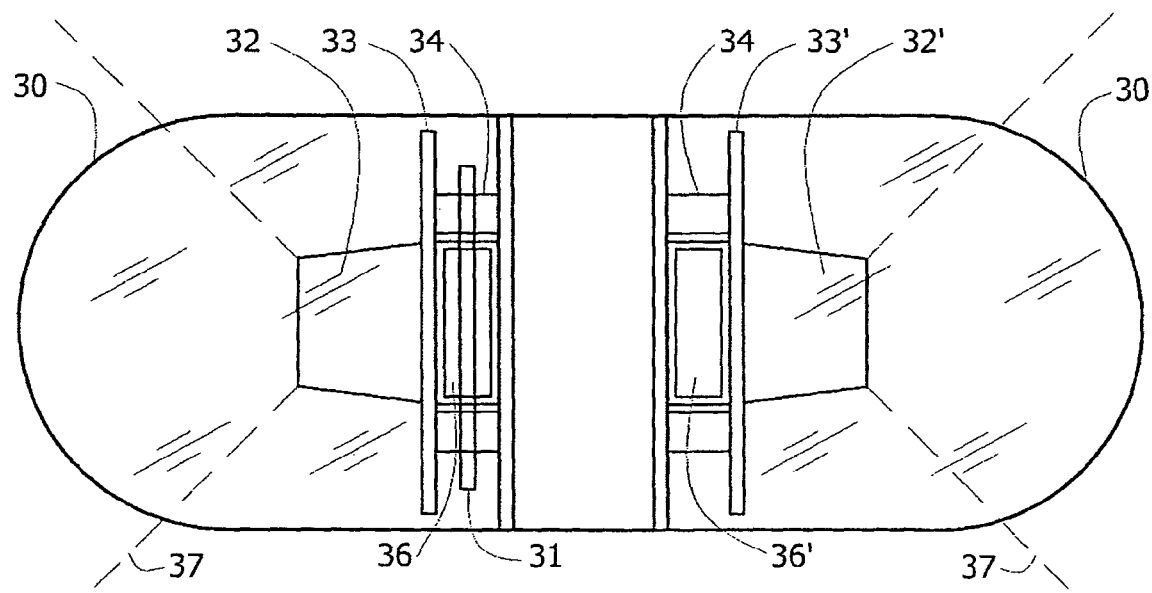

Reference is made to FIG. 1, which shows a schematic diagram of an embodiment of an in-vivo imaging device 40 and an external receiver 90 and transmitter/receiver 31 in accordance with an embodiment of the invention. In one embodiment, the system may include a device 40 having an imager 36 and/or 36' (such as for example a CMOS, a CCD, etc.), an optical system which may include lens holder 32 and/or 32', lenses and other optical elements and illumination sources 34 such as one or more LEDs (Light Emitting Diode), and/or OLEDs (Organic LED) or other suitable illumination sources. According to one embodiment the imager, optical system and light source are positioned behind a viewing window 30. Viewing window 30 may be a transparent elongated dome. The device may include a power source such as silver oxide batteries, lithium batteries, other suitable electrochemical cells having a high energy density, or the like. Other power sources may be used. For example, instead of internal power source or in addition to it, an external power source may be used to transmit power to device 40. In some embodiments, an additional sensor may be included in the device, for example, pH, temperature, pressure or other physiological parameter sensors. Other components or sensors may also be included. A processor may be included in the device which may be for example capable of processing signals that are received by device 40 into for example command or control signals that may control, activate, deactivate or otherwise alter an operative state of components that may be included in device 40. The transceiver 31 may be a transmitter or a receiver or both that may be capable of receiving wireless signals and transmitting wireless signals; in some embodiments only transmission (for example, transmission of image data from imagers 36 and/or 36') may occur. Transceiver 31 may also have other functions. In some embodiments, transceiver 31 and the processor may be or may be included in a single integrated circuit. Device 40 may include antenna that may be operably attached to transceiver 31. In some embodiments, the antenna may be used for, or in the performance of, both the receipt and transmission of wireless signals by transceiver 31. In other embodiments there may be more than one antenna. In some embodiments, device 40 may transmit but not receive signals. An additional sensor or other components need not necessarily be included.

According to one embodiment of the present invention, device 40 may include two optical units. Each optical unit may include, for example, the transparent elongated dome 30 behind which are situated illumination sources 34, lens holders 32, 32' and imager 36, 36'. According to some embodiments of the present invention, device 40 is capable of simultaneously obtaining images of the body lumen, for example, the GI tract, from two ends of the device. For example, according to one embodiment of the present invention, device 40 may be a cylindrical capsule having a front end and a rear end, which is capable of passing the entire GI tract. The front and rear ends may define a longitudinal direction and a longitudinal axis of the device 40. The lens holders 32, 32' and imagers 36, 36' may be located along the longitudinal axis. The imagers 36, 36' may be perpendicular to the longitudinal axis. The system in a cylindrical capsule can image the GI tract in the front and in the rear of the capsule. The images may be transmitted simultaneously or serially and may be displayed separately or as a single combined image.

When used herein, terms like top, bottom, front, rear, over, above, etc., are considered relative terms descriptive of, for example, when the imaging device 40 is in a specific orientation relative to the viewer or the relative position of components of the device.

According to some embodiments of the present invention, the device 40 may include one or more light blockers such as light blockers 33 and 33' which may include a suitable structure to reduce backscatter. In some embodiments, the light blocker may be formed and/or shaped such that it blocks stray light from reaching and/or flooding the imagers, such as imager 36 and imager 36'.

According to some embodiments the optical system in the device 40 may enable a wide field of view 37.

External to device 40 may be the receiver 90 and possibly a transmitter. Receiver 90 and a possible transmitter (typically including or associated with an antenna or antenna array) may be housed or included in the same housing or unit, or may be housed in one or more separate units. For example, a transmitter and receiver may be housed in a portable unit that may be carried or worn by a patient and/or may be integrated into a transceiver.

Receiver 90 may be connected to and/or in electrical communication with a processor 92 which may process, for example, data signals such as, for example, sensory or image data signals that are received from device 40 and/or control data received from device 40. In some embodiments, receiver 90 may be operably connected to a monitor/display 93 and/or a storage system 91 that may display and/or store the image or other sensory data collected and transmitted by device 40. Processor 92 may analyze data received by receiver 90 and may be in communication with storage system 91, transferring image data (which may be stored and transferred as for example frame data) or other data to and from storage system 91. Processor 92 may also provide the analyzed data to display 93 where a user may view the images. Display 93 may present or display the data such as, for example, image frame data or video data of, for example, the gastro-intestinal (GI) tract or other body lumen. In one embodiment, processor 92 may be configured for real time processing and/or for post processing to be performed. Other monitoring and receiving systems may be used.

A transmitter may typically be connected to and/or in electrical communication with processor 92. Processor 92 may function, at least partially as a controller and/or include, for example, a controller to process, for example, control commands to device 40 via the transmitter. In other embodiments of the present invention, signals other than control commands may be processed by processor 92 with, for example, the controller and transmitted via the transmitter. In yet other embodiments, the controller and processor may be separate units that may be in electrical communication with each other. In some embodiments of the present invention, control commands generated, for example, by the controller may be based on data received by the receiver 90 and processed by processor 92. In other embodiments, control commands generated, by the controller may be based on, user input data, for example, a patient or external operator may for example, initiate the transmission of a wireless signal and/or command from, for example, the transmitter to transceiver 31. In yet other embodiments, control commands may be based on both user input data and data receiver and/or processed by processor 92.

In some embodiments, transceiver 31 may be a half duplex transceiver where the transceiver 31 alternates from transmitting to receiving, e.g. via time division multiple access (TDMA). Typically, the transmission rate to the external receiver 90 may be significantly higher than the transmission rate from external transmitter to the transceiver 31. For example, device 40 may transmit, e.g. image frame data to external receiver 90 at a rate of 1-10 Mbits/s, e.g. 2.7 Mbits/s, while the external transmitter may transmit control commands to the transceiver 31 that may be at rate of 10-30 Kbits/sec.

Figure 2:
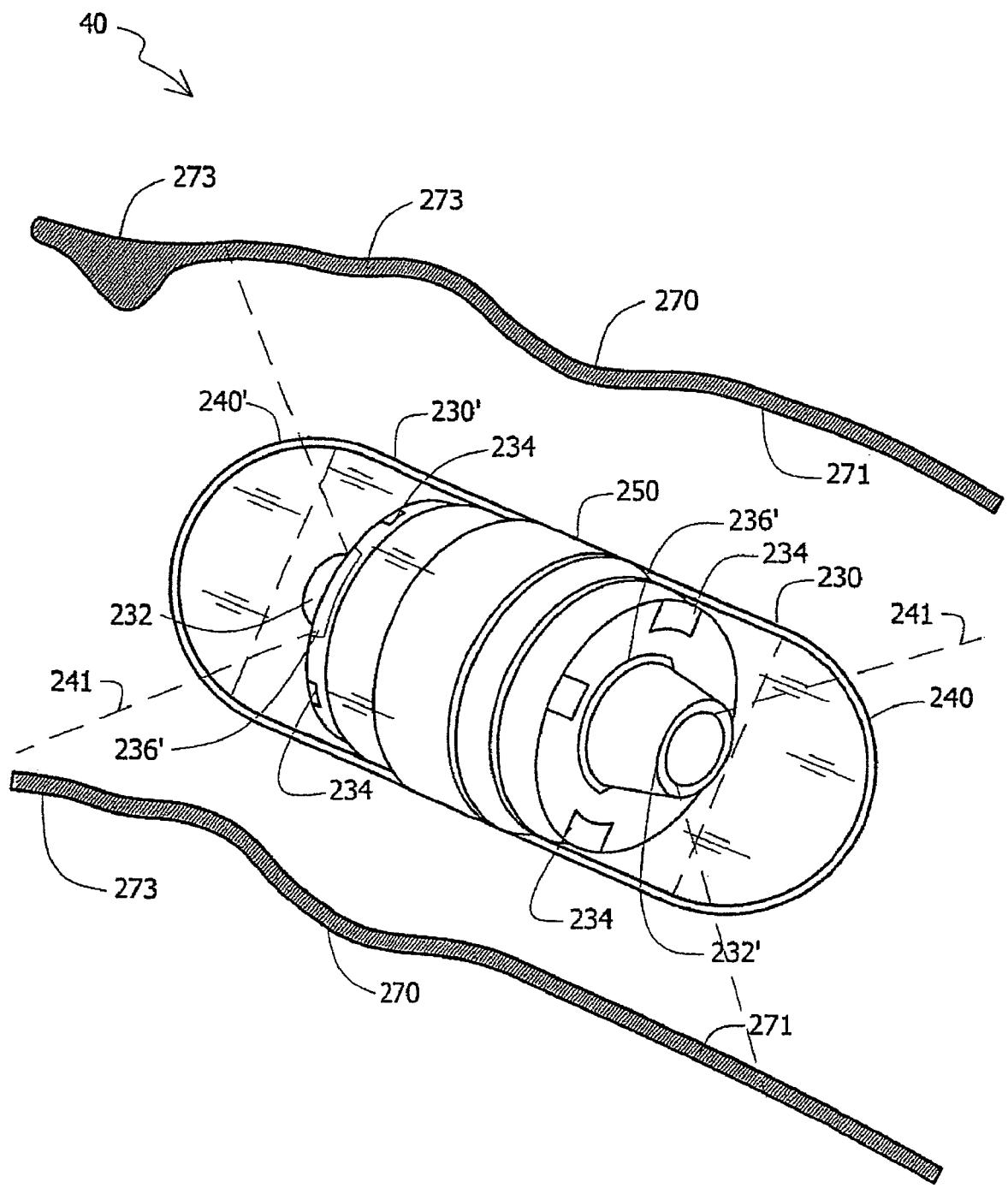
FIG. 2 schematically illustrates a perspective view of an in vivo imaging device according to some embodiments of the present invention in a body lumen.

FIG. 2 is a schematic illustration of in-vivo imaging device 40 in accordance with some embodiments of the present invention. According to one embodiment of the present invention, device 40 may be partially or entirely transparent. For example, device 40 may include areas, such as a front and rear transparent optical domes 230 and 230', which may allow components inside device 40 to have an un-obstructed field-of-view of the environment external to device 40. Other shaped transparent areas may be used. The front and rear transparent optical domes 230 and 230' may define a longitudinal direction and a longitudinal axis of the device 40.

According to one embodiment of the present invention, each of the transparent domes 230 and 230' may, respectively, include viewing windows 240 and 240'. According to some embodiments of the present invention the viewing windows 240 and 240' may for example be transparent to the light emitted by illumination sources 234 that is reflected back off of, for example, an endo-luminal wall to device 40. According to some embodiments of the present invention, the transparent domes 230 and 230' may be configured such that an appropriate field of view and/or field of illumination of the body lumen walls may be achieved with a reduced risk of stray light or backscatter from illumination sources 234 onto imagers 236 and 236'. The imagers 236, 236' may be located along the longitudinal axis and may be perpendicular thereto. According to some embodiments of the present invention the two viewing windows 240 and 240' may be configured such that a field of view 241 in the range of between 80-150 degrees is enabled; other suitable fields of view may be used. According to one embodiment of the present invention the effective focal distance (also referred to as the effective focal length), of the device 40 may typically be between 0 to 40 mm; however, other suitable distances may be used.

In one embodiment, as device 40 traverses body lumen 270, device 40 may capture images substantially simultaneously of one or more areas of body lumen 270, such as locations 271 and 273. According to some embodiments of the present invention illumination sources 234 may illuminate locations 271 and 273 of body lumen 270. The light from illuminated locations 271 and 273 may be reflected, focused and/or transferred using the optical system which may include lens holders 232 and 232', and received by imagers 236 and 236', which may thereby capture an image of locations 271 and 273. The lens holders 232, 232' may be located along the longitudinal axis.

Figure 3:
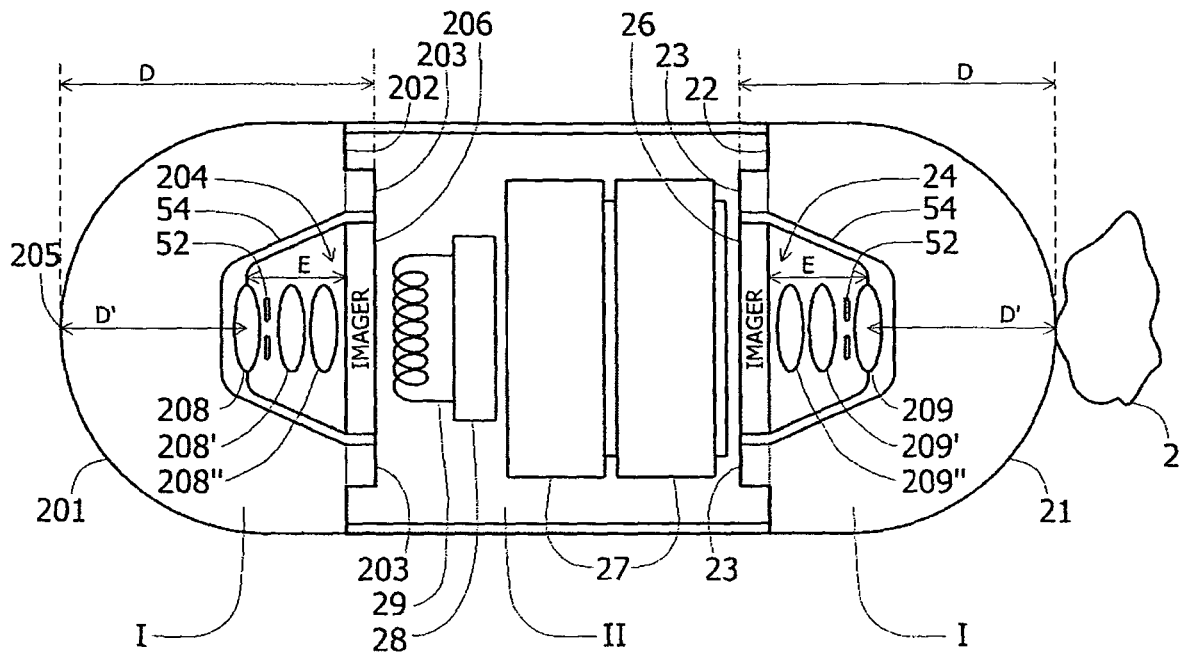
FIG. 3 schematically illustrates a longitudinal cross section of an in vivo imaging device according to some embodiments of the present invention.

Reference is made to FIG. 3, which shows a schematic representation of a longitudinal cross-section of device 40 according to embodiments of the present invention. The device 40 may include a power source 27, a transmitter 28, and an antenna 29. An optical path, in the present invention, may be the course followed by light rays incident on an in-vivo item or area within the body lumen and re-transmitted or reflected from the in-vivo item or area onto an imager 26 or 206. The optical paths may further include an objective lens (also sometimes referred to as a focusing lens) and optionally more lenses, such as a field lens. Device 40 may include, an optical system 24, 204 including, for example, a lens holder 34, one or more optical lenses 209 and/or 208, 209' and/or 208' and 209" and/or 208" having an aperture stop 52 sandwiched or otherwise disposed between the one or more optical lenses, for example, between lenses 208 and 208' and/or between lenses 209 and 209'. The one or more optical lenses may be of material such as for example ZEONEX™ synthetic resins, COC plastic, PMMA, etc. Such material may provide improved optical quality, stability during production, and better transparency. The lenses may typically direct and focus the re-transmitted or reflected light rays onto the imager 26 and/or 206. The optical system 24, 204 may typically include a lens holder 54. The lens holder 54 may keep the top lens 208, 209 in place and may hold the imager 26, 206. In a preferred embodiment, the lens holder 54 may be locked into place by anyone of the lenses 208, 208', 208"; 209, 209', 209" for example by being snapped into position at the top lens (objective lens) 208, 209. According to some embodiments the device 40 may include light blockers 22 and 202. The light blockers 22 and 202 and lens holders 54 may be coated with a reflective material so as to redirect illumination to a desired direction and away from the imager 26 or 206, for example, by centering lenses 208", 209". The lens holder 54 may further be used for centering the optical system over the image sensor 26 or 206. The lens holder 54 may be moved during the soldering of the image sensor 26 or 206 to a Printed Circuit Board (PCB) during manufacture of the device. The aperture stop 52 may include prongs or thorns to securely fix the aperture stop 52 in place when sandwiched between two lenses, however other suitable methods may be used. A desired depth of view (DOV) may be obtained by adjusting the aperture size. Different DOV may be needed depending on the body lumen that the imaging device 40 such as for example an ingestible capsule may be located within. The aperture size may typically have a substantial affect on the F-number, which is the ratio of focal length of a lens to diameter of an associated aperture. The F-number is a parameter that characterizes the amount of light allowed to enter the optical system 24, 204 and onto the imager 26 or 206. A larger aperture size may essentially increase the amount of light entering the optical system 24, 204 (decrease the F-number) and onto the imager but decrease the DOV while a smaller aperture size may increase the F-number and increase the DOV. A larger aperture size may be used when the imaging device 40 is designed to image a voluminous body lumen such as for example the colon or stomach, while a smaller aperture may be used for imaging within a smaller body lumen such as for example a small intestine.

Some embodiments of the in-vivo imaging device 40 for enhanced imaging of body lumens may include an elongated optical domes 21, 201, each having a tip 205. The elongated optical domes 21, 201 may define a longitudinal axis of the in-vivo imaging device 40 and each tip may be located on the longitudinal axis. The lenses 208, 208', 208"; 209, 209', 209" and the aperture stop 52 may be located on, and distributed along, the longitudinal axis. While two domes and associated optical systems are shown, one may also be used. The elongated optical domes 21, 201 have a longitudinal dimension defined by a distance D from each tip 205 to an associated imager 26, 206. The imagers 26, 206 may be located along the longitudinal axis and may be perpendicular thereto. The distance D may typically be at least twice the length E of an associated lens holder 54. A further distance D' is defined by the distance between the tip 205 of the optical dome 21 (or 201) to its associated optical system 24 (or 204), or more precisely, D' is the distance between the tip of the dome 21 (or 201) and the objective lens 209 (or 208). The distance D' may be an important parameter in the design of the optical system. A wide FOV (Field Of View) may be attained, inter alia, due to the combination of the following attributes that are included within some embodiments of the invention: the use of one or more lenses, elongated optical domes 21, 201, one or more illumination sources located at a substantial distance from the tip of the optical dome, and the optical system having optical paths located a substantial distance from the optical dome. For an imaging device traveling through a voluminous body lumen such as for example the stomach or colon, the FOV and DOV may be improved by the illumination sources 23 and 203 providing lighting to a larger in-vivo area due to the distance D. Since the illumination sources 23 and 203 may be positioned at the back of each optical dome 21 and 201, a greater in-vivo area may be illuminated. According to some embodiments distance D' may be equal or greater than 6 times the effective focal length of the optical system 24, 204, i.e., D'$\geq$6f. The elongated optical domes 21 and 201 may be for example hemispherically shaped optical domes 21 and 201 having optical properties that are taken into account when designing the optical systems 24 and 204 such as for example determining the spacing between the objective lens 208, 209 and field lens 208", 209". More than one feature from different embodiments may be combined in one embodiment. One imager and imaging system may be used.

Figure 4:
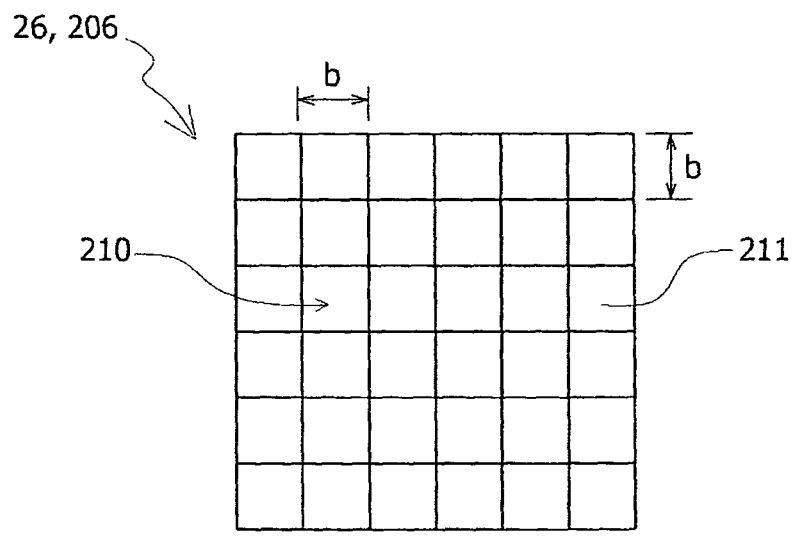
FIG. 4 schematically illustrates a front view of an imager according to some embodiments of the present invention.

The shape of the elongated optical domes 21 and 201 may be optimized to provide the necessary distance D and/or D' for adequate lighting of the in-vivo area and necessary optical characteristics for adequate focus to achieve a wide field of view (FOV) and large depth of view (DOV). In accordance with some embodiments, properties of the imager 26, 206 and/or of the lenses 208, 208', 208"; 209, 209', 209" may be adjusted in order to achieve required performance characteristics of the device 40. FIG. 4 shows a schematic illustration of imager 26, 206 having a pixel array 210, each pixel 211 having a given pixel size, b. The FOV of the device 40 depends, inter alia, on the angular coverage of each pixel 211. In accordance with some embodiments the ratio of the pixel size, b, to the focal length, f, of the optical system 24, 204 equals 0.001 radians, that is, b/f=0.01 radians. In accordance with some embodiments b/f may be in the range from 0.01-

0.0015 to 0.01+0.0015 radians, that is, b/f may be in the range 0.0085 to 0.0115. In a non-limiting and non-binding example, b=10 microns and f=1 mm.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. An in-vivo imaging device comprising:
    at least one imager and an associated optical system, at least the optical system located in an optical dome of the imaging device, the optical dome having a tip, the optical system comprising at least a first optical lens and a second optical lens, the optical system having a given effective focal length f;
    wherein the first optical lens is an objective lens and is located at the distance D' from the tip; and
    wherein $D' \geq 6f$.

2. The device according to claim 1, wherein the at least one imager comprises a pixel array, each pixel having a given pixel size, b, wherein b/f=0.01 radians.

3. The device according to claim 1, wherein the at least one imager comprises a pixel array, each pixel having a given pixel size, b, wherein b/f is in the range 0.01-0.0015 to 0.01+0.0015 radians.

4. The device according to claim 1, wherein the optical system further comprises a third optical lens and an aperture stop.

5. The device according to claim 4, wherein the aperture stop is located between the first and second optical lenses and the third optical lens is located between the second optical lens and the at least one imager.

* * * * *